United States Patent
Alsberg et al.

(10) Patent No.: US 11,191,871 B2
(45) Date of Patent: Dec. 7, 2021

(54) PARTICULATE COATED HYDROGEL MICROPARTICLES

(71) Applicant: CASE WESTERN RESERVE UNIVERSITY, Cleveland, OH (US)

(72) Inventors: Eben Alsberg, Cleveland, OH (US); Rui Tang, Solon, OH (US)

(73) Assignee: CASE WESTERN RESERVE UNIVERSITY, Cleveland, OH (US)

( * ) Notice: Subject to any disclaimer, the term of this patent is extended or adjusted under 35 U.S.C. 154(b) by 0 days.

(21) Appl. No.: 16/371,806

(22) Filed: Apr. 1, 2019

(65) Prior Publication Data

US 2019/0298656 A1    Oct. 3, 2019

Related U.S. Application Data

(60) Provisional application No. 62/650,611, filed on Mar. 30, 2018.

(51) Int. Cl.

| | |
|---|---|
| *A61L 27/24* | (2006.01) |
| *A61K 9/50* | (2006.01) |
| *A61K 47/02* | (2006.01) |
| *A61K 47/42* | (2017.01) |
| *C07K 14/78* | (2006.01) |
| *A61L 27/54* | (2006.01) |
| *C12N 5/00* | (2006.01) |
| *A61L 27/36* | (2006.01) |
| *B82Y 5/00* | (2011.01) |
| *B82Y 40/00* | (2011.01) |
| *C08J 3/075* | (2006.01) |

(52) U.S. Cl.
CPC ........... *A61L 27/24* (2013.01); *A61K 9/5084* (2013.01); *A61K 47/02* (2013.01); *A61K 47/42* (2013.01); *A61L 27/36* (2013.01); *A61L 27/54* (2013.01); *C07K 14/78* (2013.01); *C12N 5/0068* (2013.01); *B82Y 5/00* (2013.01); *B82Y 40/00* (2013.01); *C08J 3/075* (2013.01); *C08J 2389/00* (2013.01); *C12N 2533/54* (2013.01)

(58) Field of Classification Search
None
See application file for complete search history.

(56) References Cited

U.S. PATENT DOCUMENTS

2014/0170224 A1*  6/2014  Li ...................... A61K 9/5057
                                                            424/492

FOREIGN PATENT DOCUMENTS

WO            90/10454 A1    9/1990

OTHER PUBLICATIONS

Liu, H., et al., Fabrication of novel core-shell hybrid alginate hydrogel beads, International Journal of Pharmaceutics 35 1 (2008)104-112.*
Zhou, H., et al., Poly (vinyl alcohol)/SiO2 composite microsphere based on Pickering emulsion and its application in controlled drug release, Journal of Biomaterials Science, Polymer Edition, vol. 25, No. 7, 641-656.*
Gao, Q., et al., Suspension polymerization based on inverse Pickering emulsion droplets for thermo-sensitive hybrid microcapsules with tunable supracolloidal structures, Polymer 50 (2009) 2587-2594.*
Narayani, R., Panduranga, R., Gelatin microsphere cocktails of different sizes for the controlled release of anticancer drugs, International Journal of Pharmaceutics 143 (1996) 255-258.*
Cha C., et al., Microfluidics-Assisted Fabrication of Gelatin-Silica Core-Shell Microgels for Injectable Tissue Constructs, Biomacromolecules 2014, 15, 283-290; Jan. 20, 2020 IDS.*
Dang, et al., "Controlled Dual Growth Factor Delivery From Microparticles Incorporated Within Human Bone Marrow-Derived Mesenchymal Stem Cell Aggregates for Enhanced Bone Tissue Engineering via Endochondral Ossification", Stem Cells TranslationalMedicine 2016;5:206-217.
Zwiorek, et al., "Gelatin Nanoparticles as Delivery System for Nucleotide-Based Drugs", 2006.
Yanagisawa, et al., "Multiple patterns of polymer gels in microspheres due to the interplay among phase separation, wetting, and gelation", PNAS, vol. 111, Nov. 11, 2014, pp. 15894-15899.
Huang, et al., "Synthesis of uniform core-shell gelatin-alginate microparticles as intestine-released oral delivery drug carrier", Electrophoresis 2014, 35, 330-336.
Cha, et al., "Microfluidics-Assisted Fabrication of Gelatin-Silica Core-Shell Microgels for Injectable Tissue Constructs", Biomacromolecules 2014, 15, 283-290.
Hyashi, et al., "Preparation of stem cell aggregates with gelatin microspheres to enhance biological functions", 2011.
First Named Inventor: Eben Alsberg; U.S. Appl. No. 16/107,756, filed Aug. 21, 2018; NonFinal Office Action; dated Aug. 26, 2020; 16 pgs.
First Named Inventor: Eben Alsberg; U.S. Appl. No. 16/107,774, filed Aug. 21, 2018; NonFinal Office Action; dated Sep. 17, 2020; 16 pgs.
First Named Inventor: Eben Alsberg; U.S. Appl. No. 16/726,375, filed Dec. 24, 2019; NonFinal Office Action; dated Oct. 5, 2020.
Applicant: Case Western Reserve University, et al.; European Patent Application No. 17879074.7, Filing Date: Dec. 11, 2017; Communication pursuant to Article 94(3) EPC; dated Jul. 20, 2020; 10 pgs.
Chelsea S. Bahney, et al., "Stem Cell-Derived Endochondral Cartilage Stimulates Bone Healing by Tissue Transformation", Journal of Bone and Mineral Research, vol. 29, No. 5, Apr. 22, 2014, pp. 1269-1282.
Chelsea S. Bahney, et al., "The Multifaceted Role of the Vasculature in Endochondral Fracture Repair", Frontiers in Endocrinology, vol. 6, Feb. 5, 2015 (Feb. 5, 2015), p. 4.

(Continued)

*Primary Examiner* — H. Sarah Park
(74) *Attorney, Agent, or Firm* — Tarolli, Sundheim, Covell & Tummino LLP

(57) ABSTRACT

A composition includes a plurality of particulate coated hydrogel microparticles, each of the microparticles including a hydrogel inner core and a particulate shell defined by a plurality of solid nanoparticles, the particulate shell inhibiting aggregation of the microparticles in an aqueous medium and being permeable to allow release of agents from the hydrogel inner core.

17 Claims, 6 Drawing Sheets

(56) References Cited

OTHER PUBLICATIONS

Dazai S, et al., "Leukemia inhibitory factor enhances bone formation in calvarial bone defect", The Journal of Craniofacial Surgery, Nov. 2000, vol. 11, No. 6, Nov. 2000, pp. 513-520.
Guihard P, et al., "Induction of osteogenesis in mesenchymal stem cells by activated monocytes/macrophages depends on Oncostatin M signaling", vol. 50, May 2012.
Italian Patent Office, Document No. 102011902009885A1, (Bionest Ltd), Jul. 1, 2013 (Jul. 1, 2013).
L. Yang, et al., "Hypertrophic chondrocytes can become osteoblasts and osteocytes in endochondral bone formation", Proceedings of the National Academy of Sciences, vol. 111, No. 33, Aug. 19, 2014, p. 12097-12102.
Rachelle W. Johnson, et al., "Glycoprotein 130 (Gp130)/ interleukin-6 (IL-6) signalling in osteoclasts promotes bone formation in periosteal and trabecular bone", Bone, vol. 81, Aug. 7, 2015, pp. 343-351.
Rozen, et al., "Fracture repair: Modulation of fracture-callus and mechanical properties by sequential application of IL-6 following PTH 1-34 or PTH 28-48", IL-6 following PTH 1-34 or PTH 28-48, Bone, Pergamon Press., Oxford, GB, vol. 41, No. 3, Aug. 8, 2007, pp. 437-445.
Xin Zhou, et al., "Chondrocytes Transdifferentiate into Osteoblasts in Endochondral Bone during Development, Postnatal Growth and Fracture Healing in Mice", PLOS Genetics, vol. 10, No. 12, Dec. 4, 2014.

\* cited by examiner

PARTICULATE COATED HYDROGEL MICROPARTICLES

RELATED APPLICATION

This application claims priority from U.S. Provisional Application No. 62/650,661, filed Mar. 30, 2018, the subject matter of which is incorporated herein by reference in its entirety.

GOVERNMENT FUNDING

This invention was made with government support under Grant No. R01AR063194 and T32HL134622, awarded by The National Institutes of Health. The United States government has certain rights to the invention.

BACKGROUND

Gelatin hydrogel spheres at nano or micron sizes have been widely used as carriers for tissue engineering and drug delivery purposes. As a derivative from collagen, gelatin molecule contains abundant integrin binding sites that promote cell growth and functioning. Gelatin carriers also bear strong capability of adsorbing and releasing a variety of drug molecules with different sizes, hydrophobicities, electrical properties or affinities. For most of the applications, gelatin microspheres need to be homogeneously suspended prior to use. For example, when integrating gelatin microspheres to densely packed cells for tissue construct generation, gelatin microspheres are required to be mixed with cells for 3 dimensional (3D) constructions. However, due to strong intermolecular interactions, such as electrostatic interaction, after being placed into aqueous solutions, gelatin microspheres tend to aggregate. It is quite challenging to homogenously suspend gelatin microspheres in aqueous solution or mix them with cells. Tedious pipetting is usually performed to reduce the aggregation effect. Such problem greatly hampers the advantages of gelatin carrier in large scale use.

Traditional methods to overcome the problem of gelatin microspheres aggregation include crosslinking and coating with shells. In theory, crosslinking reduces intermolecular interactions of gelatin molecules through networking nearby molecules. In practice, crosslinking does not well prevent gelatin microspheres from aggregation. Alternatively, coating gelatin microspheres with organic and inorganic materials prevent interactions among gelatin molecules. However, for the delivery of drugs including small molecules and macromolecules, shells inhibit the penetration of payloads, resulting in insufficient loading and/or releasing.

SUMMARY

Embodiments described herein relate to compositions that can be used for bioactive agent delivery and tissue engineering, and more particularly to compositions that can provide delivery of bioactive agents in a temporally controlled or predetermined manner to cells or tissue in a variety of biomedical applications, including tissue engineering, drug discovery applications, and regenerative medicine.

In some embodiments, the composition can include a plurality of particulate coated hydrogel microparticles or microspheres. Each of the microparticles can include a hydrogel inner core and a porous particulate shell defined by a plurality of solid nanoparticles. The particulate shell can inhibit aggregation of the microparticles in an aqueous medium. Optionally, the hydrogel inner core can include one or more bioactive agents, and the particulate shell can allow release of the bioactive agents from the hydrogel inner core in a sustained, controlled, and/or predetermined manner.

The particulate coated hydrogel microparticles can be formed using a reverse Pickering emulsion process that assembles the solid particles onto outer surfaces of hydrogel microparticles of an emulsion. Advantageously, it was found that particulate coated hydrogel microparticles, which include a gelatin core and nanoparticle shell can outperform traditional gelatin microparticles both in supporting cell functions and releasing drugs. In addition, due to its ability of easily suspending in aqueous solution, the particulate coated hydrogel microparticles can be readily adopted for large scale production of tissue constructs for tissue engineering applications and for generating cell aggregates for in vitro testing of pharmaceutical agents.

In some embodiments, the microparticles can have an average diameter of about 1 μm to about 500 μm, and the nanoparticles can have an average diameter of about 50 nm to about 900 nm.

In other embodiments, the hydrogel inner core can include gelatin. The gelatin can be optionally cross-linked to control degradation of the inner core and/or diffusion or release of the bioactive agent from the inner core.

In some embodiments, the plurality of solid nanoparticles can include solid inorganic nanoparticles, such as silica nanoparticles.

The composition can also include a plurality of cells. The cells can be uniformly dispersed with the microparticles in the composition. The cells can include progenitor cells and stem cells, such as mesenchymal stem cells and cancer cells, and the composition can be used in tissue engineering application and drug discovery applications.

Other embodiments described herein relate to a method of a forming a plurality of particulate coated hydrogel microparticles. The method includes suspending a plurality of solid nanoparticles in an organic solvent. Hydrogel forming natural polymer macromers are dissolved in an aqueous solution. The aqueous solution of the hydrogel forming natural polymer macromers is added to the organic solvent containing the solid nanoparticles to form a Pickering emulsion. The Pickering emulsion includes a plurality of uniformly dispersed microparticles of the hydrogel forming polymer macromers and the solid nanoparticles coating outer surfaces of the hydrogel forming polymer macromers. The hydrogel forming polymer macromers are then solidified to form particulate coated hydrogel microsphere. The particulate coated hydrogel microparticles are then isolated from the organic solvent.

In some embodiments, particulate coated hydrogel microparticles formed by the method include a hydrogel inner core and a porous particulate shell defined by a plurality of solid nanoparticles. The particulate shell can inhibit aggregation of the microparticles in an aqueous medium and be permeable to allow release or diffusion of bioactive agents contained in the hydrogel inner core from the hydrogel inner core.

In other embodiments, the hydrogel inner core includes at least one bioactive agent. The at least one bioactive agent can be added to the hydrogel inner core during or after formation of the particulate coated hydrogel microparticles.

DETAILED DESCRIPTION

Figure 1:
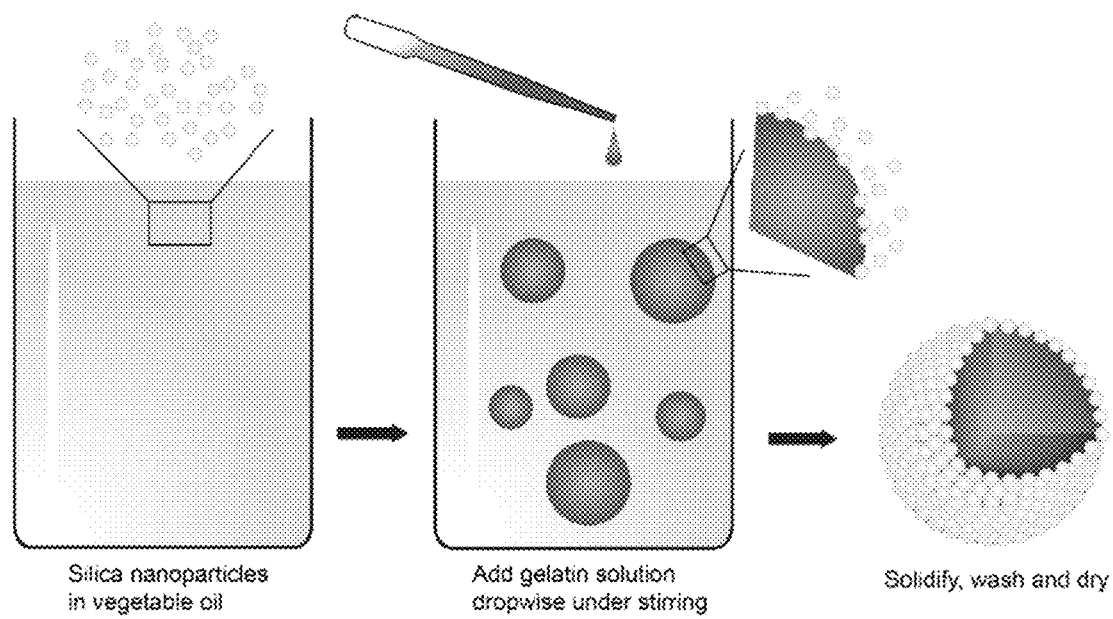
FIG. 1 illustrates a schematic showing the preparation of gelatin core/particle shell microspheres.

Methods involving conventional molecular biology techniques are described herein. Such techniques are generally known in the art and are described in detail in methodology treatises, such as *Current Protocols in Molecular Biology*, ed. Ausubel et al., Greene Publishing and Wiley-Interscience, New York, 1992 (with periodic updates). Unless otherwise defined, all technical terms used herein have the same meaning as commonly understood by one of ordinary skill in the art to which the present invention pertains. Commonly understood definitions of molecular biology terms can be found in, for example, Rieger et al., *Glossary of Genetics: Classical and Molecular*, 5th Edition, Springer-Verlag: New York, 1991, and Lewin, *Genes V*, Oxford University Press: New York, 1994. The definitions provided herein are to facilitate understanding of certain terms used frequently herein and are not meant to limit the scope of the present invention.

The term "antisense" nucleic acid refers to oligonucleotides which specifically hybridize (e.g., bind) under cellular conditions with a gene sequence, such as at the cellular mRNA and/or genomic DNA level, so as to inhibit expression of that gene, e.g., by inhibiting transcription and/or translation. The binding may be by conventional base pair complementarily, or, for example, in the case of binding to DNA duplexes, through specific interactions in the major groove of the double helix.

The term "bioactive agent" refers to any agent capable of promoting tissue formation, destruction, and/or targeting a specific disease state (e.g., cancer). When administered to a host, both human and animal, e.g., the bioactive agent may be used as part of a prophylatic or therapeutic treatment. Examples of bioactive agents can include, but are not limited to, chemotactic agents, various proteins (e.g., short term peptides, bone morphogenic proteins, collagen, glycoproteins, and lipoprotein), cell attachment mediators, biologically active ligands, integrin binding sequence, various growth and/or differentiation agents and fragments thereof (e.g., epidermal growth factor (EGF), hepatocyte growth factor (HGF), vascular endothelial growth factors (VEGF), fibroblast growth factors (e.g., bFGF), platelet derived growth factors (PDGF), insulin-like growth factor (e.g., IGF-I, IGF-II) and transforming growth factors (e.g., TGF-β I-III)), parathyroid hormone, parathyroid hormone related peptide, bone morphogenic proteins (e.g., BMP-2, BMP-4, BMP-6, BMP-7, BMP-12, BMP-13, BMP-14), transcription factors, such as sonic hedgehog, growth differentiation factors (e.g., GDF5, GDF6, GDF8), recombinant human growth factors (e.g., MP52 and the MP-52 variant rhGDF-5), cartilage-derived morphogenic proteins (CDMP-1, CDMP-2, CDMP-3), small molecules that affect the upregulation of specific growth factors, tenascin-C, hyaluronic acid, chondroitin sulfate, fibronectin, decorin, thromboelastin, thrombin-derived peptides, heparin-binding domains, heparin, heparan sulfate, polynucleotides, DNA fragments, DNA plasmids, MMPs, TIMPs, interfering RNA molecules, such as siRNAs, oligonucleotides, proteoglycans, glycoproteins, glycosaminoglycans, and DNA encoding for shRNA. In addition, biological entities, such as viruses, virenos, and prions are considered bioactive agents. The bioactive agents may be water-soluble or water-insoluble and may include those having a high molecular weight, such as proteins, peptides, carbohydrates and glycoproteins.

The term "biocompatibility" or "biocompatible" when used in relation to microparticles or microspheres described herein refers to microparticles or microspheres that are neither themselves toxic to the host (e.g., an animal or human), nor degrade (if at all) at a rate that produces byproducts at toxic concentrations in the host. To determine whether any subject microparticles are biocompatible, it may be necessary to conduct a toxicity analysis. Such assays are well known in the art.

The term "biodegradable" refers to those embodiments in which microparticles or hydrogels described herein are intended to degrade during use. In general, degradation attributable to biodegradability involves the degradation of a microsphere or hydrogel into its constituents and encapsulated materials. The degradation rate of a biodegradable microsphere or hydrogel often depends in part on a variety of factors, including the identity of any constituents that form the microsphere and hydrogel and their ratio, the identity and loading of any material (including bioactive agent encapsulated in a microsphere), how any microsphere may be crosslinked and to what extent. For example, a microsphere that is crosslinked will, in all likelihood, degrade more slowly than one that is not crosslinked.

The term "cell" can refer to any progenitor cell, such as totipotent stem cells, pluripotent stem cells, and multipotent stem cells, as well as any of their lineage descendant cells, including more differentiated cells. The terms "stem cell" and "progenitor cell" are used interchangeably herein. The cells can derive from embryonic, fetal, or adult tissues. Exemplary progenitor cells can be selected from, but not restricted to, totipotent stem cells, pluripotent stem cells, multipotent stem cells, mesenchymal stem cells (MSCs), hematopoietic stem cells, neuronal stem cells, hematopoietic stem cells, pancreatic stem cells, cardiac stem cells, embryonic stem cells, embryonic germ cells, neural crest stem cells, kidney stem cells, hepatic stem cells, lung stem cells, hemangioblast cells, and endothelial progenitor cells, cancer stem cells. Additional exemplary progenitor cells are selected from, but not restricted to, de-differentiated chondrogenic cells, chondrogenic cells, cord blood stem cells, multi-potent adult progenitor cells, myogenic cells, osteogenic cells, tendogenic cells, ligamentogenic cells, adipogenic cells, and dermatogenic cells.

When used with respect to the bioactive agent, the term "controlled release" is intended to mean that the bioactive agent is released over time in contrast to a bolus type administration in which the entire amount of the bioactive agent is presented to the target at one time. The release will vary as explained below.

The term "gene" or "recombinant gene" refers to a nucleic acid comprising an open reading frame encoding a polypeptide, including both exonic and (optionally) intronic sequences.

The term "gene construct" refers to a vector, plasmid, viral genome or the like which includes an "coding sequence" for a polypeptide or which is otherwise transcribable to a biologically active RNA (e.g., antisense, decoy, ribozyme, etc.), can transfect cells, preferably mammalian cells, and can cause expression of the coding sequence in cells transfected with the construct. The gene construct may include one or more regulatory elements operably linked to the coding sequence, as well as intronic sequences, polyadenylation sites, origins of replication, marker genes, etc.

The term "host cell" or "target cell" refers to a cell transduced with a specified transfer vector. The cell is optionally selected from in vitro cells such as those derived from cell culture, ex vivo cells, such as those derived from an organism, and in vivo cells, such as those in an organism.

The term "incorporated" or "encapsulation," when used in reference to a bioactive agent or other material and a microsphere, denotes formulating a bioactive agent or other material into a microsphere useful for controlled release of such agent or material. As used herein, those terms contemplate any manner by which a bioactive agent is incorporated into a microsphere, including for example: distributed throughout the matrix, appended to the surface of microparticles, and encapsulated inside the matrix or microparticles. The term "coincorporation" or "coencapsulation" as used herein refers to the incorporation of a bioactive agent in a microsphere and at least another bioactive agent or other material.

The term "microspheres", "microdroplets", or "microparticles" are used interchangeably and refer to substantially spherical structures formed by a coacervation process. The microdroplets generally have a matrix-type structure, and can incorporate and/or encapsulate a bioactive agent within the matrix. The microparticles generally have a size distribution within the range of from about 1 μm to about 500 μm. In certain embodiments, over 90% of the microparticles formed in a single preparation of microparticles have a diameter in excess of about 5 μm. Other sizes are also contemplated herein When a large number of microparticles are formed, they may have a variable size. In certain embodiments, the size distribution may be uniform, e.g., within less than about a 20% standard deviation of the median volume diameter, and in other embodiments, still more uniform or within about 10% of the median volume diameter.

The term "modulation" refers to both up regulation (i.e., activation or stimulation) and down regulation (i.e., inhibition or suppression) of a response.

The term "nucleic acid" refers to polynucleotides, such as deoxyribonucleic acid (DNA), and, where appropriate, ribonucleic acid (RNA). The term should also be understood to include, as equivalents, analogs of either RNA or DNA made from nucleotide analogs, and, as applicable to the embodiment being described, single-stranded (such as sense or antisense) and double-stranded polynucleotides. Exemplary nucleic acids for use in the subject invention include antisense, decoy molecules, recombinant genes (including transgenes) and the like.

The phrases "parenteral administration" and "administered parenterally" means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intra-articulare, subcapsular, subarachnoid, intraspinal and intrasternal injection and infusion.

The phrase "pharmaceutically acceptable" refers to those microparticles and dosages thereof within the scope of sound medical judgment, suitable for use in contact with the tissues of human beings and animals without excessive toxicity, irritation, allergic response, or other problem or complication, commensurate with a reasonable benefit/risk ratio.

The term "prophylactic or therapeutic" treatment refers to administration to the host of the subject micro and/or nanodroplets. If it is administered prior to clinical manifestation of the unwanted condition (e.g., disease or other unwanted state of the host animal) then the treatment is prophylactic, i.e., it protects the host against developing the unwanted condition, whereas if administered after manifestation of the unwanted condition, the treatment is therapeutic (i.e., it is intended to diminish or ameliorate the existing unwanted condition or side effects therefrom).

The terms "protein," "polypeptide" and "peptide" are used interchangeably when referring to a gene product.

"Recombinant host cells" refers to cells which have been transformed or transfected with vectors constructed using recombinant DNA techniques.

The terms "recombinant protein," "heterologous protein" and "exogenous protein" are used interchangeably to refer to a polypeptide which is produced by recombinant DNA techniques, wherein generally, DNA encoding the polypeptide is inserted into a suitable expression vector which is in turn used to transform a host cell to produce the heterologous protein. That is, the polypeptide is expressed from a heterologous nucleic acid.

As used herein, the term "subject" can refer to any animal, including, but not limited to, humans and non-human animals (e.g., rodents, arthropods, insects, fish (e.g., zebrafish), non-human primates, ovines, bovines, ruminants, lagomorphs, porcines, caprines, equines, canines, felines, ayes, etc.), which is to be the recipient of a particular treatment. Typically, the terms "patient" and "subject" are used interchangeably herein in reference to a human subject.

The phrases "systemic administration," "administered systemically," "peripheral administration" and "administered peripherally" mean the administration of a subject supplement, composition, therapeutic or other material such that it enters the patient's system and, thus, is subject to metabolism and other like processes, for example, subcutaneous administration.

The phrase "therapeutically effective amount" means that amount of a bioactive agent that, when present in a microsphere, produces some desired effect at a reasonable benefit/risk ratio applicable to any medical treatment. In certain embodiments, a therapeutically effective amount of a bioactive agent for in vivo use will likely depend on a number of factors, including: the rate of release of the bioactive agent from the microsphere, which will depend in part on the chemical and physical characteristics of the such microsphere, the identity of the bioactive agent, the mode and method of administration; any other materials incorporated in the microsphere in addition to the bioactive agent.

The term "treating" as used herein is intended to encompass curing as well as ameliorating at least one symptom of any condition or disease.

Embodiments described herein relate to compositions that can be used for bioactive agent delivery and tissue engineering, and more particularly to compositions that can provide delivery of bioactive agents in a temporally controlled or predetermined manner to cells or tissue in a variety of biomedical applications, including tissue engineering, drug discovery applications, and regenerative medicine.

In some embodiments, the composition can include a plurality of particulate coated hydrogel microparticles. Each of the microparticles can include a hydrogel inner core and a porous particulate shell defined by a plurality of solid nanoparticles. The particulate shell can inhibit aggregation of the microparticles in an aqueous medium. Optionally, the hydrogel inner core can include one or more bioactive agents, and the particulate shell can allow release or diffusion of the bioactive agents from the hydrogel inner core in a sustained, controlled, and/or predetermined manner.

The particulate coated hydrogel microparticles can be formed using a reverse Pickering emulsion process that assembles the solid particles such that they are adsorbed onto outer surfaces of hydrogel microparticles of an emulsion. A "reverse Pickering emulsion" or a "water in oil Pickering emulsion" refers to an emulsion that utilizes solid particles as a stabilizer to stabilize droplets of a water soluble organic substance, such as the gel forming natural polymer macromers described below, in a dispersed phase in the form of microdroplets or microparticles dispersed throughout a continuous phase, which comprises an organic solvent or oil medium. As used herein, the term "adsorbed" refers to the adherence of atoms, ions, or molecules of a gas or liquid to the surface of another substance by a relatively small force, such as a force on the order of van der Waals forces, as opposed to a chemical reaction or covalent bond.

Advantageously, it was found that particulate coated hydrogel microparticles, which include a gelatin core and nanoparticle shell can outperform traditional gelatin microparticles both in supporting cell functions and releasing drugs. In addition, due to its ability of easily suspending in aqueous solution, the particulate coated hydrogel microparticles can be readily adopted for large scale production of tissue constructs for tissue engineering applications and for generating cell aggregates for in vitro testing of pharmaceutical agents.

In some embodiments, the hydrogel inner core can include a natural polymer macromer that is soluble in an aqueous solution and can form a hydrogel upon gelation. The natural polymer macromer can be substantially cytocompatible (i.e., substantially non-cytotoxic) and have controllable physical properties, such as degradation rate, swelling behavior, and mechanical properties. Examples of natural polymer macromers include collagen, gelatin, glycosaminoglycans (GAG), poly (hyaluronic acid), alginate, hyaluronan, agarose, polyhydroxybutyrate (PHB), and combinations thereof.

The natural polymer macromers used to form the hydrogel microparticles may be cross-linked with a cross-linking agent in order to enhance the mechanical strength of the microparticles and/or control physical properties of the microparticles, such as degradation rate, swelling behavior. Examples of cross-linking agents may include divalent cations, genipin, glutaraldehyde, tri-polyphosphate (TPP), hydroxyapitite (HA), and any other cross-linking agent known to those skilled in the art. By way of example, the natural polymer macromer can include gelatin The natural polymer macromer (e.g., gelatin) can also be acrylated and/or methacrylated by reacting an acryl group and/or methacryl a natural polymer macromer (e.g., gelatin). For example, bovine type-B gelatin can be dissolved in a phosphate buffered solution and then reacted with methacrylic anhydride to provide a plurality of methacrylate groups on the gelatin.

The degree of acrylation and/or methacrylation can be controlled to control the degree of subsequent crosslinking of the acrylate and methacrylates as well as the mechanical properties, and biodegradation rate of the gelatin. The degree of acrylation or methacrylation can be about 1% to about 99%, although this ratio can vary more or less depending on the end use of the composition.

In some embodiments, the acrylate or methacrylate groups of the acrylated and/or methacrylated natural polymer macromer can be crosslinked by photocrosslinking using UV light in the presence of photoinitiators. For example, acrylated and/or methacrylated natural polymer macromers can be photocrosslinked in an appropriate amount of diH$_2$O or aqueous media (e.g., PBS) containing a desired amount of a photoinitiator.

The photoinitiator can include any photo-initiator that can initiate or induce polymerization of the acrylate or methacrylate macromer. Examples of the photoinitiator can include camphorquinone, benzoin methyl ether, 2-hydroxy-2-methyl-1-phenyl-1-propanone, diphenyl(2,4,6-trimethylbenzoyl)phosphine oxide, benzoin ethyl ether, benzophenone, 9,10-anthraquinone, ethyl-4-N,N-dimethylaminobenzoate, diphenyliodonium chloride and derivatives thereof.

The acrylated and/or methacrylated natural polymer macromers can be exposed to a light source at a wavelength and for a time to promote crosslinking of the acrylate and/or methacrylate groups of the macromers.

In some embodiments, microspheres generally have one or more dimensions of less than about 1000 µm, for example less than about 500 µm, for example, less than about 250 µm. In other embodiments, the hydrogel microparticles can have an average diameter of about 1 µm to about 500 µm, about 25 µm to about 400 µm, or about 50 µm to 200 µm.

The solid nanoparticles used to define the porous particulate shell surrounding the hydrogen inner core can include any solid nanoparticle that can be readily adsorbed onto the interphase between two phases of an emulsion, such an oil/water interface, to reduce overall interfacial energy of the emulsion system and stabilize the emulsion. In some embodiments, the porous particulate shell comprises a monolayer of inorganic nanoparticles. The inorganic nanoparticles can be metal nanoparticles, metal alloy nanoparticles, metal oxide nanoparticles, or a combination thereof.

The nanoparticles generally have one or more dimensions of less than about 1000 nanometers, for example less than about 500 nanometers, for example, less than about 250 nanometers. For example, the nanoparticles can have an average diameter of about 1 nm to about 999 nm. In some embodiments, the nanoparticles are spherical nanoparticles. In some embodiments, the nanoparticles are silica nanoparticles, silicon nanoparticles, gold nanoparticles, titanium oxide nanoparticles, and the like, or a combination thereof. In other embodiments, the nanoparticles comprise silica, titanium dioxide, or a combination thereof. In some embodiments, the inorganic nanoparticles comprise silica, for example, the inorganic nanoparticles can be silica nanoparticles. In some embodiments, the inorganic nanoparticles have an average diameter of about 1 nm to about 999 nm, about 50 nm to about 900 nm, about 75 nm to 800 nm, or about 100 nm to 750 nm, or about 200 nm to about 700 nm.

The Pickering emulsion used to form the particulate coated hydrogel microparticles can be prepared by suspending a plurality of solid nanoparticles in an organic solvent, such as a plant derived oil, such as vegetable oil or olive oil, that does not dissolve the hydrogen forming natural polymer macromers. The hydrogel forming natural polymer macromers are dissolved in an aqueous solution.

The aqueous solution of the hydrogel forming natural polymer macromers is then gently added to the organic solvent containing the solid nanoparticles. The added solution of natural polymer macromers forms droplet in the organic solvent. The solid nanoparticles in the organic solvent (e.g., oil) move to the organic solvent/water interface to form a reverse Pickering emulsion.

The mixture is agitated under shearing forces to reduce the size of droplets. During this time an equilibrium of the Pickering emulsion is reached and the size of the droplets is stabilized by the action of the solid nanoparticles in coating the surface of the droplets of the natural polymer macromer solution. The Pickering emulsion includes a plurality of uniformly dispersed microparticles of the hydrogel forming polymer macromers and the solid nanoparticles coating outer surfaces of the hydrogel forming polymer macromers in a substantially continuous layer. The substantially continuous layer means that the solid nanoparticles form a porous coating on the surface of the microparticles or microdroplets of natural polymer macromer solution that is sufficiently continuous enough to prevent coalescence of the microspheres or microdroplets within the organic solvent.

The emulsion can then be gelated by, for example, reducing the temperature of the system to the gelation temperature of the hydrogel forming polymer macromers. The hydrogel forming polymer macromers are then solidified to form particulate coated hydrogel microparticles by extracting water from the emulsion. The water can be extracted from the emulsion by adding a third solvent that is miscible or substantially miscible with both the organic solvent and water and which does not dissolve the hydrogel forming polymer macromers. The particulate coated hydrogel microparticles are then isolated from organic solvent by filtration and washing with the filtered particulate coated microparticles with the third solvent to remove the organic solvent and unbound solid particles.

In certain embodiments, the Pickering emulsions described herein are substantially free or, in some cases, completely free of any surfactant. As used herein, the term "surfactant" refers to materials that have an amphiphilic molecular structure, which includes a polar hydrophilic molecular moiety and a nonpolar lipophilic molecular moiety, and which acts to lower the interfacial tension between the dispersed phase and the continuous phase in an emulsion. As will be appreciated, surfactants can be classified as ionic (anionic, cationic, and amphoteric) or nonionic. As used herein, the term "substantially free" when used with reference to the absence of surfactant in the Pickering emulsions described herein, means that the emulsion comprises less than 0.05 percent by weight of surfactant, based on the total weight of the solid particle stabilizer and natural polymer macromers. As used herein, the term "completely free" when used with reference to the absence of surfactant in the Pickering emulsions described herein, means that the emulsion comprises no surfactant at all.

In some embodiments, the particulate coated hydrogel microparticles can include one more bioactive agents that can be incorporated and/or encapsulated in the hydrogel inner core of the microparticles to provide localized, sustained, and/or controlled release of the at least one bioactive agents to cells in or about the microparticles under physiological conditions in a controlled or predetermined manner. By incorporating and/or encapsulating bioactive agent in a microsphere microdroplet, it is possible, in certain embodiments, to provide a steady dosage of such bioactive agent through a sustained or controlled release process. In addition, such encapsulation may protect the bioactive agent, or other materials from undesirable immunogenic, proteolytic or other events that would reduce the efficacy of the bioactive agent and may regulate immunogenic, proteolytic, or other events.

The at least one bioactive agent can include polynucleotides and/or polypeptides encoding or comprising, for example, transcription factors, differentiation factors, growth factors, and combinations thereof. The at least one bioactive agent can also include any agent capable of promoting tissue formation (e.g., bone and/or cartilage), destruction, and/or targeting a specific disease state (e.g., cancer). Examples of bioactive agents include chemotactic agents, various proteins (e.g., short term peptides, bone morphogenic proteins, collagen, glycoproteins, and lipoprotein), cell attachment mediators, biologically active ligands, integrin binding sequence, various growth and/or differentiation agents and fragments thereof (e.g., EGF), HGF, VEGF, fibroblast growth factors (e.g., bFGF), PDGF, insulin-like growth factor (e.g., IGF-I, IGF-II) and transforming growth factors (e.g., TGF-β I-III), parathyroid hormone, parathyroid hormone related peptide, bone morphogenic proteins (e.g., BMP-2, BMP-4, BMP-6, BMP-7, BMP-12, BMP-13, BMP-14), sonic hedgehog, growth differentiation factors (e.g., GDF5, GDF6, GDF8), recombinant human growth factors (e.g., MP-52 and the MP-52 variant rhGDF-5), cartilage-derived morphogenic proteins (CDMP-1, CDMP-2, CDMP-3), small molecules that affect the upregulation of specific growth factors, tenascin-C, hyaluronic acid, chondroitin sulfate, fibronectin, decorin, thromboelastin, thrombin-derived peptides, heparin-binding domains, heparin, heparan sulfate, polynucleotides, DNA fragments, DNA plasmids, MMPs, TIMPs, interfering RNA molecules, such as siRNAs, DNA encoding for an shRNA of interest, oligonucleotides, proteoglycans, glycoproteins, and glycosaminoglycans.

The bioactive agents can be loaded, incorporated, and/or encapsulated into hydrogel microparticles during their preparation. For example, the bioactive agent can be initially combined with the hydrogel forming natural polymer macromer prior to mixing with the organic solvent so that the bioactive agent is provided in the hydrogel microspheres. Alternatively or additionally, the at least on bioactive agent can be combined with the particulate coated hydrogel microparticles after formation and/or isolation by mixing the particulate coated hydrogel microparticles in a solution containing bioactive agent.

The amount of bioactive agent provided in the microparticles will depend on a number of factors, including: (i) the identity of the bioactive agent; (ii) the microsphere's intended use, including any desired therapeutic effect for in vivo use; (iii) the chemical and physical properties of the microsphere, including the release rate of encapsulated bioactive agent or other material under different conditions.

In certain embodiments, a sufficient amount of the bioactive agent can be incorporated into the microparticles to produce a therapeutically beneficial result. In those embodiments in which the bioactive agent is a polypeptide, such as BMP-2 or TGF-β, the polypeptide loaded in any microsphere may range from less than about 0.05 to more than about 50 weight percent, or about 0.1, 0.25, 0.5, 0.75, 1.0, 1.5, 2.0, 3.0, 4.0, 5.0, 6.0, 7.0, 8.0, 9.0, 10, 15, 20, 25, 30, 35, 40, or 45 weight percent.

In addition to bioactive agents, other materials may be incorporated into the microparticles. Such additional materials may affect the therapeutic and other characteristics of the microsphere that results. One example of such another material is an adjuvant. (Such materials may also be termed bioactive agents if appropriate.)

Alternatively, materials that augment the therapeutic effect of the bioactive agent may be incorporated into the microparticles. For example, natural polymers, such as heparin, that control and/or delay the release of the bioactive agent can be provided in the microsphere. (Such materials may also be referred to as bioactive agents as appropriate). The amount of any such augmenting agent to be loaded into any microsphere will depend on a variety of factors, including the nature of the such agent, the microsphere, whether there are any other materials incorporated in addition to the bioactive agent, and the like. For any such agent, the present invention contemplates incorporating a sufficient amount to augment the therapeutic effect of the bioactive agent. In other embodiments, the amount of such augmenting agent may range from about 0.005% up to about 25%, or alternatively 0.01, 0.05, 0.1, 0.25, 0.5, 1.0, 2.5, 5.0, 10, 15 or 20%.

In some embodiments, more than two different bioactive agents can be loaded into the microparticles. In certain embodiments, three, four, five or more bioactive agents augmenting agents, fillers or other materials may be incorporated in any microsphere microdroplet and/or hydrogel.

The release rate of the bioactive agent from the microparticles micro will vary with different embodiments. For example, one subject formulation may require at least an hour to release a major portion of the bioactive agent into the surrounding medium, whereas another formulation may require about 1-24 hours, or even much longer. In certain embodiments, such release may result in release (over, say 1 to about 2,000 hours, or alternatively about 2 to about 800 hours) of the bioactive agent or other material encapsulated in the microparticles. In certain embodiments, such substance or other material may be released in an amount sufficient to produce a therapeutically beneficial response.

The release profile of any bioactive agent or other material from the microparticles may vary in different embodiments. In one embodiment, the bioactive agent or other material is released from the microparticles in a pulsatile manner. For example, such a pulsatile manner may involve release of the bioactive agent or other material in three phases: an initial burst, a slow release, and a second burst. In another embodiment, the bioactive agent or other material is released in a sustained manner. In still other embodiments, a significant portion of the bioactive agent or other material is released in an initial phase. In still other embodiments, the release profile is bi-phasic or multi-phasic.

In some embodiments, solid particles of particulate shell can substantially prevent release of the bioactive agent from the microparticles for a certain time period and then allow release of the bioactive agent thereafter, and the delayed release can be adjusted to the time necessary for the compositions to reach the desired location. The solid particles that form the porous particulate shell can be configured or selected so that diffusion or release of the bioactive agent from the inner core may be delayed or sustained.

Delayed release can be for a time of about 1 hr or greater, about 2 hrs or greater, about 4 hrs or greater, about 8 hrs or greater, about 12 hrs or greater, about 24 hrs or greater, about 2 days or greater, about 3 days or greater, about 4 days or greater, about 5 days or greater, about 1 week or greater, or about 2 weeks or greater. In each instance, the maximum time of delayed release can be about 3 weeks, about 4 weeks, or about 6 weeks. In particular embodiments, delayed release can be a time of about 1 hr to about 1 week, about 2 hrs to about 5 days, about 4 hrs to about 2 days, or about 8 hrs to about 24 hrs. Sustained release can be calculated from the time bioactive agent release begins, from the time of first delivery of the microparticles, or from the time that the microparticles first encounter the conditions of the desired delivery location.

In some embodiments, release can be delayed as noted above and also be sustained once release begins. Sustained release can proceed for a time of about 12 hrs or greater, about 24 hrs or greater, about 2 days or greater, about 3 days or greater, about 4 days or greater, about 5 days or greater, about 1 week or greater, or about 2 weeks or greater. In each instance, the maximum duration of sustained release can be about 3 weeks, about 4 weeks, about 6 weeks, or about 12 weeks. In particular embodiments, sustained release can be a time of about 12 hrs to about 6 weeks, about 24 hrs to about 4 weeks, or about 2 days to about 2 weeks.

In other embodiments, the controlled release of the bioactive agent can be controlled by controlling the degree or amount of cross-linking of hydrogel inner core. For example, the hydrogel inner core of the microparticles can be configured to one or more labile crosslinking groups. The crosslinking groups can maintain the hydrogel microsphere configuration until contact with a material and/or condition adapted to break the crosslinks.

In some embodiments, the particulate coated hydrogel microparticles can provide localized, sustained, and/or controlled release of the at least one bioactive agents to cells in or about the microparticles in a controlled or predetermined manner. For example, a plurality of cells can be mixed with hydrogel microparticles that include a bioactive agent, and the bioactive agent can be controllably release in a spatial or temporal manner to facilitate proliferation, growth, and/or differentiation of the cells. The cells can include any cell, such as progenitor cells, totipotent stem cells, a pluripotent stem cells, or a multipotent stem cells, differentiated cells, cancer cells as well as any of their lineage descendant cells, including more differentiated cells (described above), such as MSCs and cancer stem cells.

The cells can be autologous, xenogeneic, allogeneic, and/or syngeneic. Where the cells are not autologous and are potentially administered to a subject for therapeutic applications, it may be desirable to administer immunosuppressive agents in order to minimize immunorejection. The cells employed may be primary cells, expanded cells, or cell lines, and may be dividing or non-dividing cells. Cells may be expanded ex vivo prior to combination or mixing with the hydrogel. For example, autologous cells can be expanded in this manner if a sufficient number of viable cells cannot be harvested from the host subject. Alternatively or additionally, the cells may be pieces of tissue, including tissue that has some internal structure. The cells may be primary tissue explants and preparations thereof, cell lines (including transformed cells), or host cells.

Generally, cells can be combined with the particulate coated hydrogel microparticles in vitro, although in vivo seeding approaches can optionally or additionally be employed. If the mixture of particulate coated hydrogel microparticles and cells is to be implanted for use in vivo after in vitro seeding, for example, sufficient growth medium may be supplied to ensure cell viability during in vitro culture prior to in vivo application. Once the mixture has been implanted, the nutritional requirements of the cells can be met by the circulating fluids of the host subject.

Alternatively or additionally, cells may be layered on the particulate coated hydrogel microparticles, or the particulate coated hydrogel microparticles may be added to a cell suspension and allowed to remain there under conditions and for a time sufficient for the cells to incorporate within or attach to the microsphere hydrogel. Generally, it is desirable to avoid excessive manual manipulation of the cells in order to minimize cell death. For example, in some situations it may not be desirable to manually mix or knead the cells with the hydrogel microparticles; however, such an approach may be useful in those cases in which a sufficient number of cells will survive the procedure.

As those of ordinary skill in the art will appreciate, the number of cells to be mixed with the particulate coated hydrogel microparticles will vary based on the intended application of the hydrogel and on the type of cell used. Where dividing cells are being introduced by mixing with the particulate coated hydrogel microparticles, for example, a lower number of cells can be used. Alternatively, where non-dividing cells are mixed with the particulate coated hydrogel microparticles, a larger number of cells may be required.

In another embodiment, particulate coated hydrogel microparticles may contain particles useful to locate the microsphere for diagnostic applications and the like. In certain embodiments, particulate coated hydrogel microparticles may contain paramagnetic, superparamagnetic or ferromagnetic substances which are of use in magnetic resonance imaging (MRI) diagnostics. For example, submicron particles of iron or a magnetic iron oxide may be incorporated into particulate shell or hydrogel inner core to provide ferromagnetic or superparamagnetic particles. Paramagnetic MRI contrast agents principally comprise paramagnetic metal ions, such as gadolinium ions, held by a chelating agent which prevents their release (and thus substantially reduces their toxicity). In another embodiment, microsphere micro and/or nanodroplets and/or hydrogels may contain submicron particles, such as magnetic iron oxide, which permit the magnetic separation of microparticles. Other labeled compounds, such as radionucleides, e.g., $^3$H, $^{14}$C, $^{18}$F, $^{32}$P, $^{99m}$Tc, and $^{125}$I, may also be utilized for visualizing cells and tissues, to which microsphere micro and/or nanodroplets and/or hydrogels may be bound, by means of X-rays or magnetic resonance imaging. The particulate coated hydrogel microparticles may also contain in certain embodiments, ultrasound contrast agents, such as heavy materials, e.g., barium sulphate or iodinated compounds, to provide ultrasound contrast media.

In still other embodiments, the particulate coated hydrogel microparticles may be conjugated to targeting molecules attached to the surface of the particulate shell or the inner hydrogel core, such as monoclonal antibodies that preferentially bind to a receptor or other site of interest. In certain embodiments, such targeting may achieve targeted delivery in vivo of the particulate coated hydrogel microparticles. To attach targeting molecules to the surface of any particulate coated hydrogel microsphere, it may be necessary to provide s linker molecules. Such linker molecules may be used to attach targeting molecules. Alternatively, the constituents that form the particulate hydrogel microsphere, e.g., hydrogel, solid particles, and/or bioactive agent, may contain functional groups that allow for attachment of targeting molecules.

The particulate coated hydrogel microparticles can be injectable and/or implantable, and can be provided in a solution or carrier vehicle. The particulate coated hydrogel microparticles can be used in a variety of biomedical applications, including tissue engineering, drug discovery applications, and regenerative medicine and cancer therapy.

In one example, a composition comprising suspended chondrogenic cells, such as MSCs, and particulate coated hydrogel microparticles, which include a growth factor, such as BMP-2 and/or or TGF-β, can be used in a method to promote tissue growth in a subject. One step of the method can include identifying a target site. The target site can comprise a tissue defect (e.g., cartilage and/or bone defect) in which promotion of new tissue (e.g., cartilage and/or bone) is desired. The target site can also comprise a diseased location (e.g., tumor). Methods for identifying tissue defects and disease locations are known in the art and can include, for example, various imaging modalities, such as CT, MRI, and X-ray.

The tissue defect can include a defect caused by the destruction of bone or cartilage. For example, one type of cartilage defect can include a joint surface defect. Joint surface defects can be the result of a physical injury to one or more joints or, alternatively, a result of genetic or environmental factors. Most frequently, but not exclusively, such a defect will occur in the knee and will be caused by trauma, ligamentous instability, malalignment of the extremity, meniscectomy, failed ACI or mosaicplasty procedures, primary osteochondritis dessecans, osteoarthritis (early osteoarthritis or unicompartimental osteochondral defects), or tissue removal (e.g., due to cancer). Examples of bone defects can include any structural and/or functional skeletal abnormalities. Non-limiting examples of bone defects can include those associated with vertebral body or disc injury/destruction, spinal fusion, injured meniscus, avascular necrosis, cranio-facial repair/reconstruction (including dental repair/reconstruction), osteoarthritis, osteosclerosis, osteoporosis, implant fixation, trauma, and other inheritable or acquired bone disorders and diseases.

Tissue defects can also include cartilage defects. Where a tissue defect comprises a cartilage defect, the cartilage defect may also be referred to as an osteochondral defect when there is damage to articular cartilage and underlying (subchondral) bone. Usually, osteochondral defects appear on specific weight-bearing spots at the ends of the thighbone, shinbone, and the back of the kneecap. Cartilage defects in the context of the present invention should also be understood to comprise those conditions where surgical repair of cartilage is required, such as cosmetic surgery (e.g., nose, ear). Thus, cartilage defects can occur anywhere in the body where cartilage formation is disrupted, where cartilage is damaged or non-existent due to a genetic defect, where cartilage is important for the structure or functioning of an organ (e.g., structures such as menisci, the ear, the nose, the larynx, the trachea, the bronchi, structures of the heart valves, part of the costae, synchondroses, enthuses, etc.), and/or where cartilage is removed due to cancer, for example.

After identifying a target site, such as a cranio-facial cartilage defect of the nose, the composition comprising suspended chondrogenic cells, such as MSCs, and particulate coated hydrogel microparticles can be administered to the target site. The composition comprising suspended chondrogenic cells, such as MSCs, and particulate coated hydrogel microparticles can be prepared according to the method described above.

Next, the composition comprising suspended chondrogenic cells, such as MSCs, and particulate coated hydrogel microparticles may be loaded into a syringe or other similar device and injected or implanted into the tissue defect. Upon injection or implantation into the tissue defect, the composition can form into the shape of the tissue defect.

After implanting the composition comprising suspended chondrogenic cells, such as MSCs, and particulate coated hydrogel microparticles into the subject, the progenitor cells microparticles can migrate into the tissue defect, express growth and/or differentiation factors, and/or promote chondroprogenitor cell expansion and differentiation. Additionally, the presence of the hydrogel microparticles in the tissue defect may promote migration of endogenous cells surrounding the tissue defect.

In another example, the particulate coated hydrogel microparticles can be suspended with a plurality of cancer cells, such as cancer stem cells, for in vitro testing of pharmaceutical agents. The pharmaceutical agent can include an agent that modulates the cancer cell growth or proliferation. The pharmaceutical can be released from the hydrogel coated microparticles or administered to the cells from an external source.

The following example is for the purpose of illustration only and is not intended to limit the scope of the claims, which are appended hereto.

EXAMPLE

Pickering emulsion is a kind of emulsion that utilizes solid particles as the stabilizer. Particles are adsorbed onto the interface between the two phases of the emulsion, such as oil/water interface, to reduce the overall interfacial energy of the system and thus stabilize the emulsion. Taking advantage of Pickering emulsion mechanism, we developed a solid particle shell/gelatin core microsphere for drug delivery. In this structure, gelatin core serves as the drug carrier as traditional gelatin microsphere carriers do. The particle shell has two functions. The first function is to prevent aggregation of gelatin due to reduced interactions of gelatin molecules among different microspheres. Secondly, unlike solid surface shells, particle shell is permeable, allowing payloads to penetrate inward and outward microspheres. The microsphere can be further crosslinked by a variety of crosslinkers, such as genipin and aldehyde to increase the stability during incubation.

Preparation steps of the core/shell microspheres are schematically summarized in FIG. 1. Briefly, solid particles are firstly suspended in warm organic solvents, such as vegetable oil, and gelatin is dissolved in warm aqueous solution. Then gelatin solution is gently added into organic phase under stirring and gentle warming. After that, water-in-oil emulsion will form and solid particles will move to water/oil interface to form reversed Pickering emulsion by reducing the interfacial energy of the system. The emulsion is then gelated by reducing temperature of the system to less than 15° C. due to the gelation ability of gelatin. Water is then extracted from the microgels by adding a third solvent that can be mixed with both phases, such as acetone. Solidified microspheres are obtained by filtration and washing with the third solvent to remove organic solvent and unbound solid particles. Traditional Pickering emulsion is oil-in-water style. In current process, the phases in the system are reversed and the oil-in-water emulsion are prepared through the same mechanism.

Figure 2A:
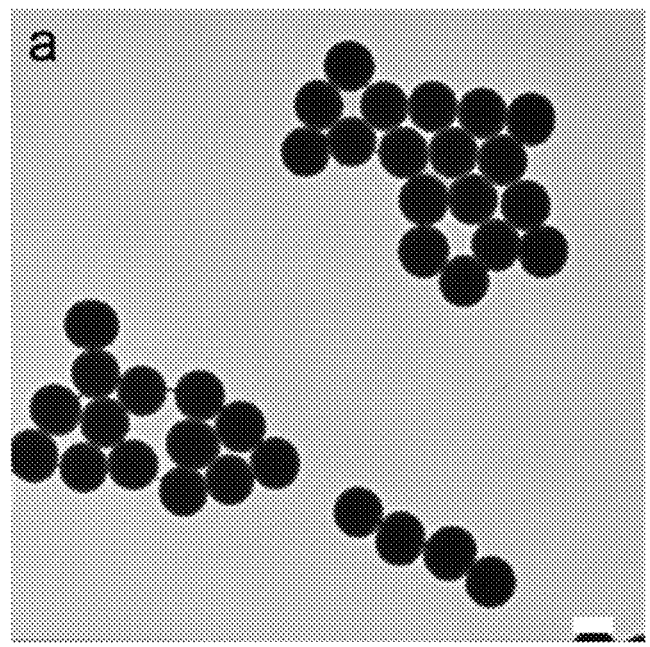
FIGS. 2(A-D) illustrate images showing core/shell microspheres have better water suspension ability. (A) Silica nanoparticles used for the assembly. Bar: 500 nm (B) 2 mg Microspheres in 1 mL water after 5 s vortexing. Left: Core/shell microspheres; Right: Gelatin microspheres without silica nanoparticles. Arrows indicate visibly aggregated microspheres. (C) Microscopic image shows 2 mg Core/shell microspheres in 1 mL water after 5 s vortexing. (D) Microscopic image shows 2 mg gelatin microspheres without silica shell in 1 mL water after 5 s vortexing. Bars: 200 μm.
Figure 2B:
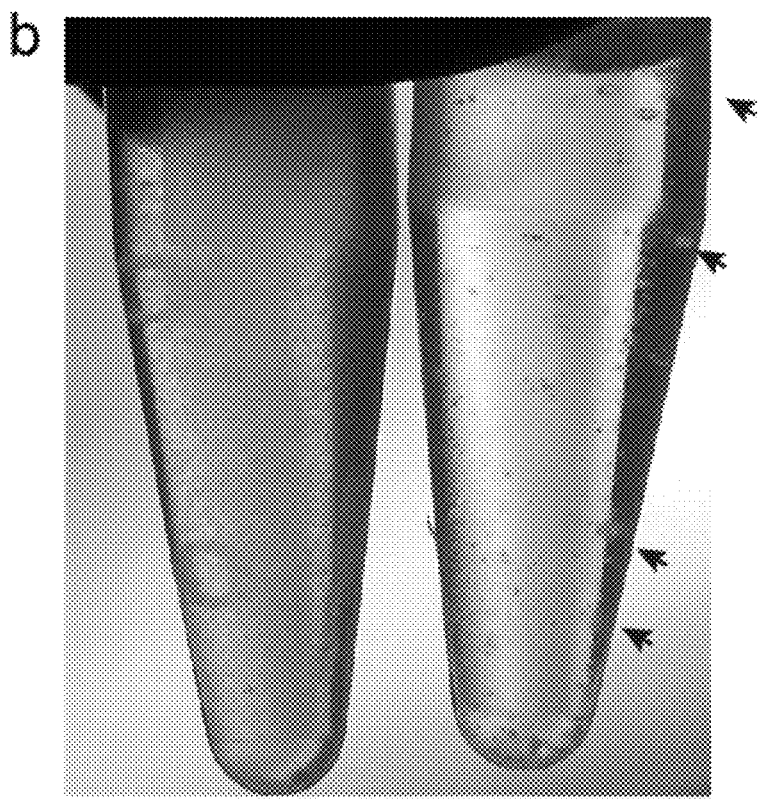
Figure 2C:
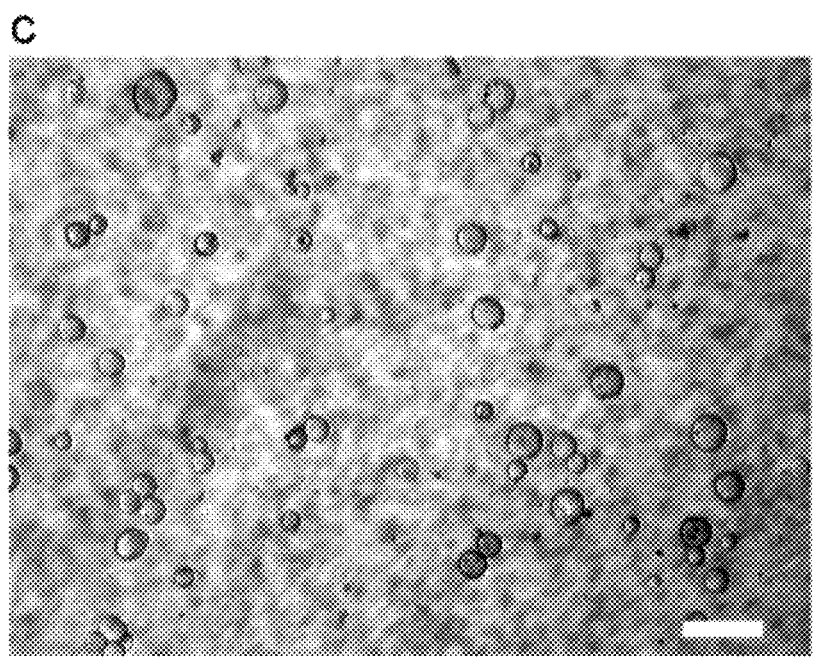
Figure 2D:
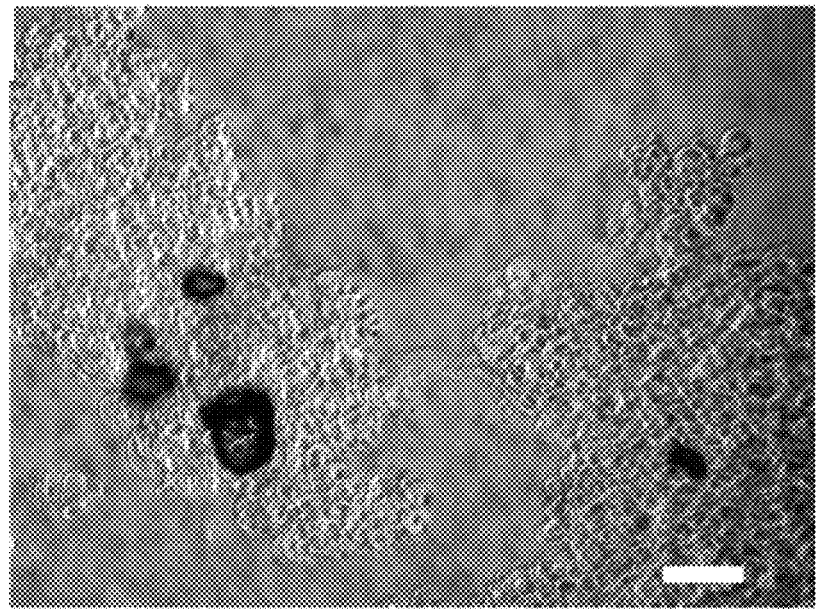

As an example, 600 nm silica nanoparticles (FIG. 2A) are used as the coating materials to make a core/shell microsphere following the above procedure. Obtained core/shell microsphere has an average size of 63±22 μm. These microspheres are easily resuspended in aqueous solution by 5 s vortexing (FIG. 2B, C). In contrast, gelatin microspheres without particle shells are quite clumpy and difficult to be resuspended under the same condition (FIG. 2B, D). It is noteworthy that silica nanoparticles can be replaced by other types of solid particles at nano or micron sizes. Properties of obtained core/shell microspheres can also be tailored by switching particle types or tuning their surface functions.

Figure 3A:
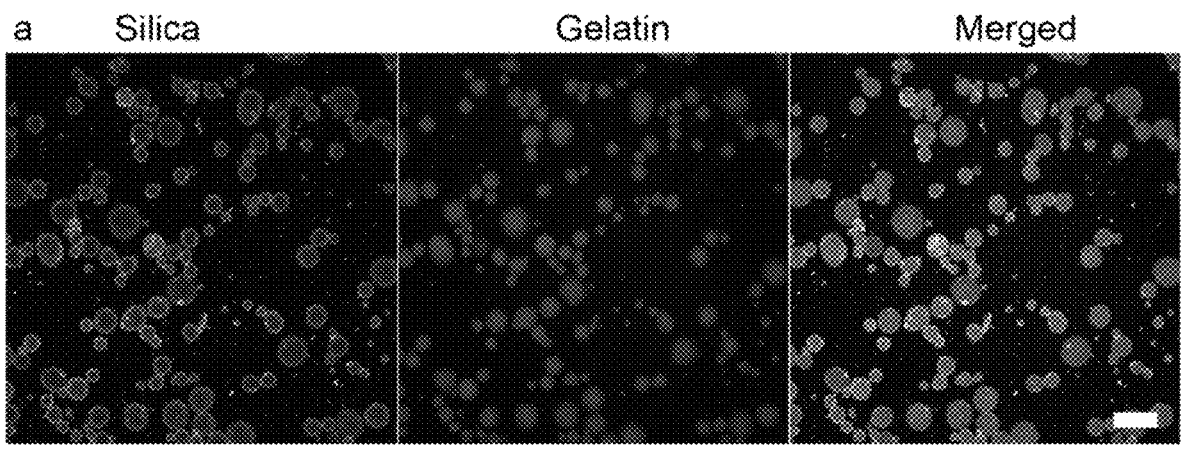
FIGS. 3(A-C) illustrate LSCM images of silica shell/gelatin core microspheres. Microspheres are squeezed by cover slips for imaging of surface coats. (A) Large scale image shows core/shell structure. Bar: 100 μm. (B) Z-stack LSCM image shows surface of microspheres. (C) Same z-stack LSCM image shows center of microspheres. Bars: 50 μm. Green: FITC labeled silica; Red: TRITC labeled gelatin.
Figure 3B:
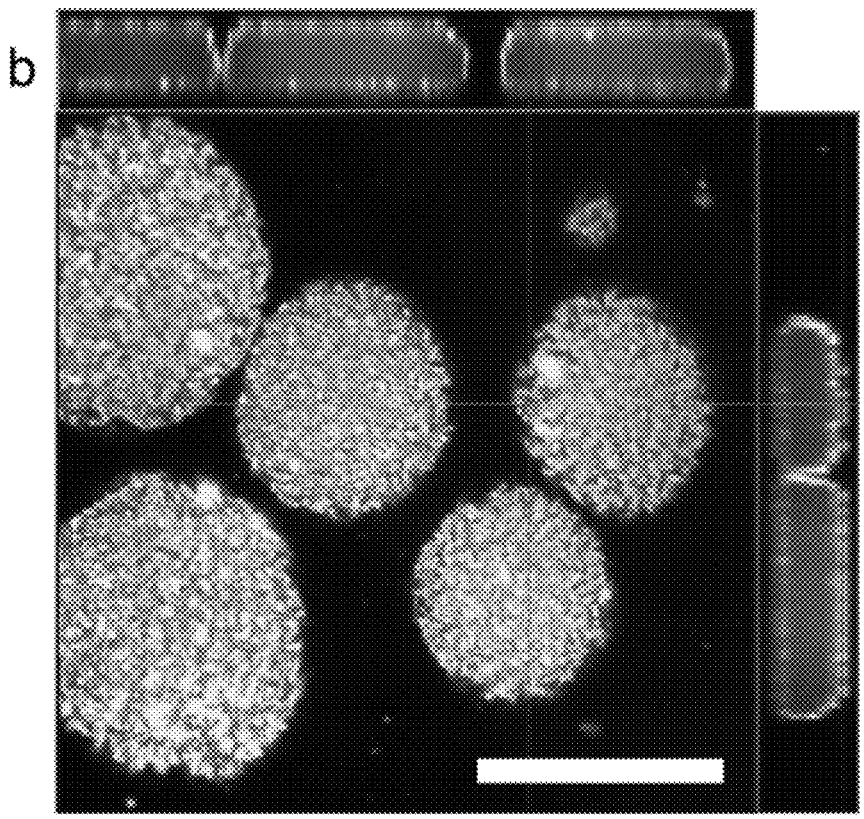
Figure 3C:
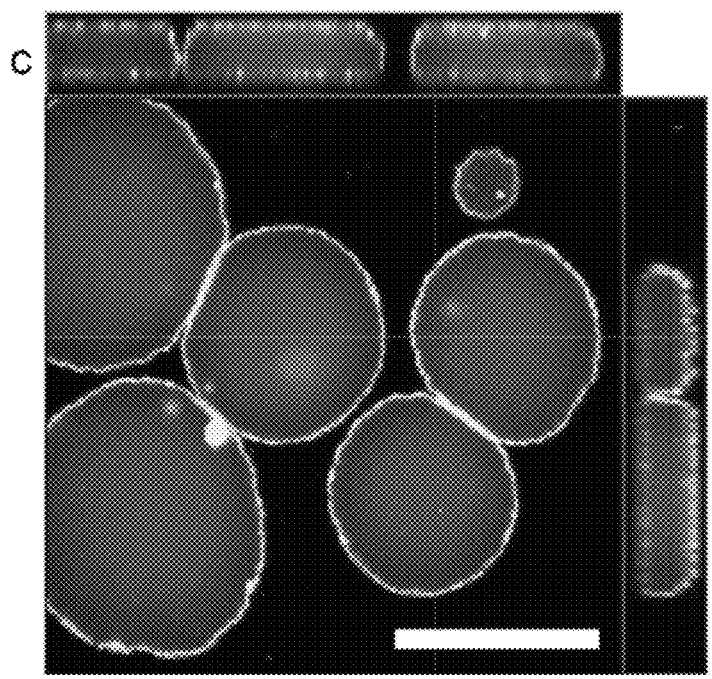

To confirm the core/shell structure, silica nanoparticles are fluorescently labeled by fluorescein isothiocyanate (FITC) and gelatin is fluorescently labeled by tetramethylrhodamine isothiocyanate (TRITC). The preparation procedure of the microsphere is the same as the one without fluorescence labels. Obtained microspheres are observed by laser scanning confocal microscopy (LSCM). To better display the shell structure, microspheres are loaded within two pieces of thin glass cover slips without spacers, so that microspheres are squeezed by the gravity of top cover slip. LSCM images (FIG. 3) clearly demonstrate that silica particles form a thin shell on the surface (green channel) and gelatin compose the core layer (red channel). The shell layer appears porous, i.e., particles are not tightly packed on the surface and gaps between silica clusters can be seen (FIG. 3B). This morphology indicates a sufficient coating with good permeability so that microspheres are readily separated in aqueous and drugs can be easily loaded or released. Microsphere cores are almost fully composed of gelatin and nearly no particles reside at the center of microspheres (FIG. 3c), indicating similar loading capability of core/shell microspheres as traditional gelatin microspheres.

Figure 4:
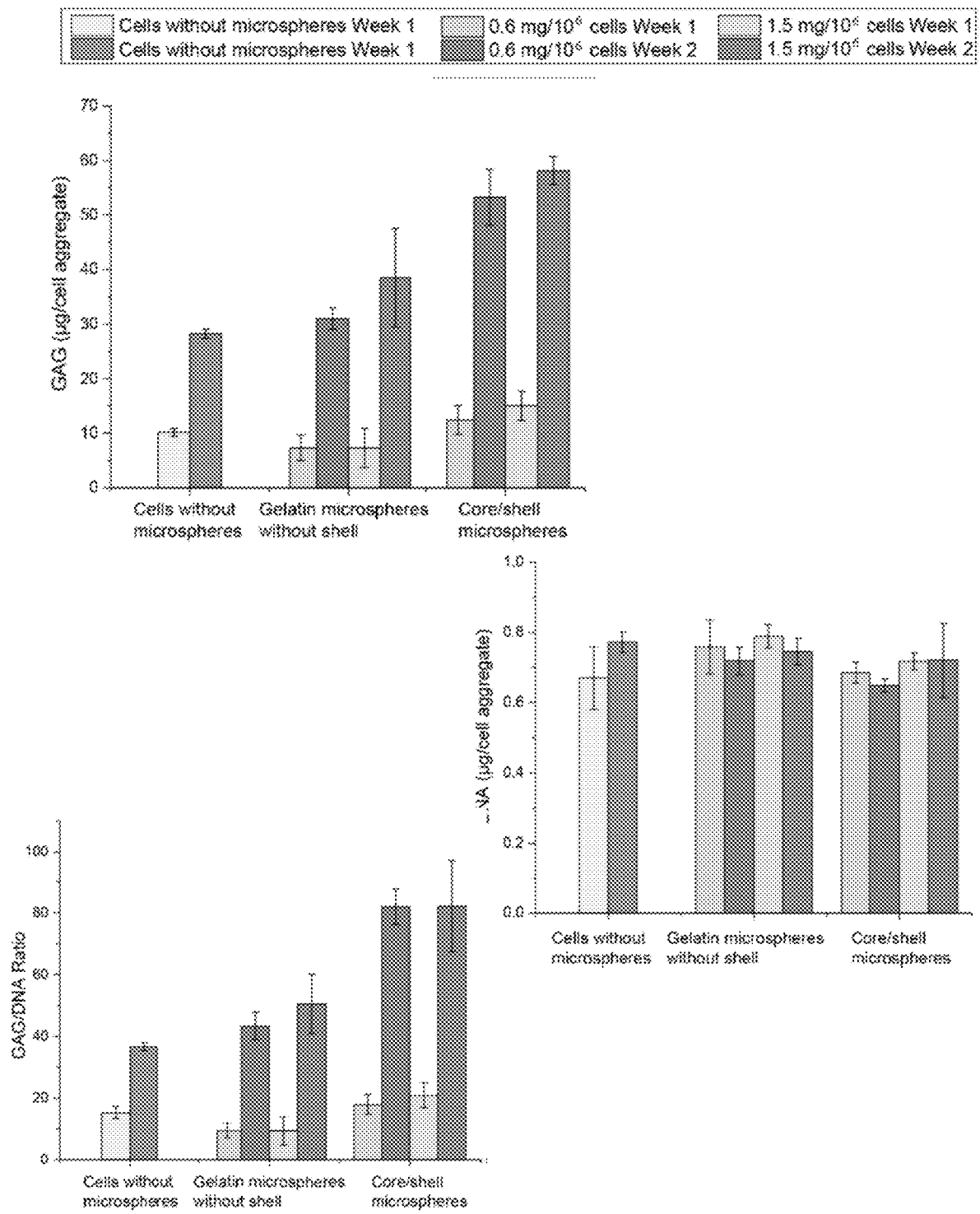
FIG. 4 illustrates graphs showing GAG and DNA content analysis of cell aggregates with exogenous TGF-β1 supply after 1 week or 2 weeks.
Figure 5:
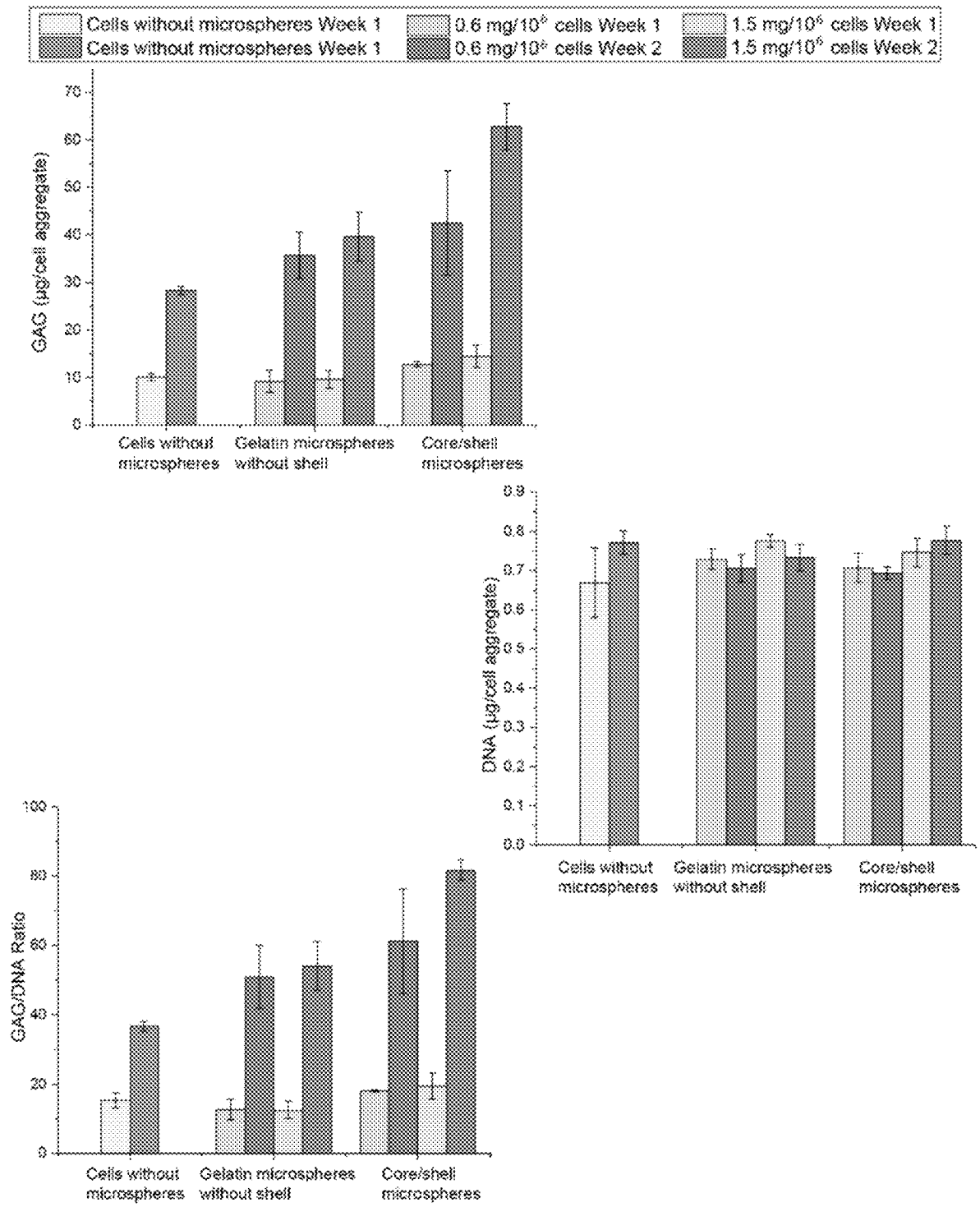
FIG. 5 illustrates graphs showing GAG and DNA content analysis of cell aggregates with endogenous TGF-β1 supply after 1 week or 2 weeks.

Gelatin core of uncrosslinked microsphere dissolves at 37° C., making it ideal for short term drug delivery purposes. For sustained delivery or long term biological support, microspheres can be crosslinked to enhance their thermostability. Crosslinkers include genipin, aldehydes, phenols and other protein crosslinking reagents. After crosslinking, microspheres can be evenly mixed with cells to extracellularly support cell survival/differentiation 12 and sustainably release drugs, or to induce cell differentiation in engineered tissue constructs. For example, after genipin crosslinking, core/shell microspheres are homogenously mixed with human mesenchymal stem cells (hMSCs) at 0.6 mg or 1.5 mg per million cells. The mixture is transferred to V-bottom nonadhesive 96 well plates at the density of 250,000 cells per well with 200 μL Chondrogenic induction media. Transforming growth factor beta 1 (TGF-β1) is exogenously supplied at 10 ng/mL. After the formation of aggregates, cells are continuously cultured for 2 weeks with media changing every 2 days. Cells without microspheres or with similar sized gelatin microspheres but without particle coating are cultured under the same condition as controls. After 2 weeks, aggregates are collected for glycosaminoglycan (GAG) and DNA assays to determine chondrogenic differentiation extent. As shown in FIG. 4, hMSCs mixed with core/shell microspheres expressed significantly higher level of GAG. DNA assay result indicates that cell numbers among different groups remain similar. After normalization of GAG level to DNA amount (GAG/DNA ratio), average GAG production level of cells mixed with core/shell microspheres is significantly higher than controls. Obviously, core/shell microsphere better supports hMSC differentiation than gelatin microsphere without particle shell or hMSC alone does. This improvement is presumably due to better cell-microsphere contact as a result of more homogenous integration of core/shell microspheres to cell constructs.

After loading drugs, core/shell microspheres can serve as a long term drug carrier. For example, after loading TGF-β1, core/shell microspheres are mixed with hMSCs as endogenous supplier of TGF-β1 for chondrogenic differentiation. Culture condition is similar to above but without exogenous support of TGF-β1. Cells without any microspheres or with same sized gelatin microspheres without particle shells were cultured under the same condition as controls. After 2 weeks culture, hMSCs mixed with core/shell microspheres expressed significantly higher level of GAG. After normalization with DNA amount, the GAG/DNA ratio is also significantly higher than controls. This result indicates that particle shell significantly enhances the long term drug supply performance of gelatin microspheres.

In summary, a novel gelatin core/solid particle shell microsphere structure is invented. This invention harnesses Pickering emulsion mechanism, assembles solid particles onto surfaces of gelatin emulsion through reverse Pickering emulsion formation process. Gelatin core/particle shell microspheres outperform traditional gelatin microspheres both in supporting cell functions and releasing drugs. In addition, due to its ability of easily suspending in aqueous solution, core/shell microspheres can be readily adopted for large scale production of tissue constructs. This technique will be particularly interesting to tissue engineering companies to make in vitro engineered tissues, and pharmaceutical companies to generate cell aggregates for in vitro testing of drugs mimicking 3D cellular environment.

From the above description of the invention, those skilled in the art will perceive improvements, changes and modifications. Such improvements, changes and modifications within the skill of the art are intended to be covered by the appended claims. All references, publications, and patents cited in the present application are herein incorporated by reference in their entirety.

Having described the invention, we claim:

1. A method of forming a plurality of particulate coated hydrogel microparticles; the method comprising:
    suspending a plurality of solid silica nanoparticles in an organic solvent;
    dissolving a hydrogel forming natural polymer macromer in an aqueous solution;
    adding the aqueous solution of the hydrogel forming natural polymer macromer to the organic solvent containing the solid silica nanoparticles to form a Pickering emulsion, wherein the Pickering emulsion includes a plurality of uniformly dispersed microparticles of the hydrogel forming natural polymer macromer and the solid silica nanoparticles coating outer surfaces of the hydrogel forming natural polymer macromer;
    solidifying the hydrogel forming natural polymer macromer by reducing the temperature of the Pickering emulsion to the gelation temperature of the hydrogel forming natural polymer macromer and extracting water from the Pickering emulsion to form particulate silica coated hydrogel microparticles; and
    isolating the particulate silica coated hydrogel microparticles from the organic solvent;
    wherein the hydrogel forming natural polymer macromer includes at least one of gelatin, collagen, alginate, agarose, or a glycosaminoglycan.

2. The method of claim 1, wherein each of the particulate silica coated hydrogel microparticles includes a hydrogel inner core and a particulate silica shell defined by a plurality of solid silica nanoparticles, the particulate silica shell inhibiting aggregation of the particulate silica coated hydrogel microparticles in an aqueous medium and being permeable to allow release of agents from the hydrogel inner core.

3. The method of claim 1, wherein the organic solvent comprises a plant derived oil.

4. The method of claim 1, wherein a solvent that is mixable with both phases of the Pickering emulsion is used to extract water from the Pickering emulsion.

5. The method of claim 1, wherein the particulate silica coated hydrogel microparticles have an average diameter of about 1 μm to about 500 μm and the silica nanoparticles have an average diameter of about 1 nm to about 999 nm.

6. The method of claim 1, wherein particulate silica coated hydrogel microparticles are isolated from the organic solvent by filtration.

7. The method of claim 1, wherein the hydrogel forming natural polymer macromer comprise gelatin.

8. The method of claim 7, wherein the gelatin is at least partially crosslinked.

9. The method of claim 2, wherein the hydrogel inner core includes at least one bioactive agent, wherein the at least one bioactive agent is added to the hydrogel inner core during or after formation of the particulate silica coated hydrogel microparticles.

10. A method of forming a tissue construct, the method comprising:
    suspending a plurality of solid silica nanoparticles in an organic solvent;
    dissolving a hydrogel forming natural polymer macromer in an aqueous solution, wherein the hydrogel forming natural polymer macromer comprises gelatin;
    adding the aqueous solution of the hydrogel forming natural polymer macromer to the organic solvent containing the solid silica nanoparticles to form a Pickering emulsion, wherein the Pickering emulsion includes a plurality of uniformly dispersed microparticles of the hydrogel forming natural polymer macromer and the solid silica nanoparticles coating outer surfaces of the hydrogel forming natural polymer macromer;
    solidifying the hydrogel forming natural polymer macromer to form particulate silica coated hydrogel microparticles; and
    isolating the particulate silica coated hydrogel microparticles from the organic solvent;
    wherein at least one bioactive agent is loaded, incorporated, and/or encapsulated into the microparticles to provide localized, sustained, and/or controlled release of the at least one bioactive agent to cells in or about the microparticles to facilitate proliferation, growth, and/or differentiation of the cells, and
    wherein the hydrogel forming polymer macromer is solidified by reducing the temperature of the Pickering emulsion to the gelation temperature of the hydrogel forming natural polymer macromer and extracting water from the Pickering emulsion to form particulate silica coated hydrogel microparticles.

11. The method of claim 10, wherein the particulate silica coated hydrogel microparticles each include a hydrogel inner core and a particulate silica shell defined by a plurality of solid silica nanoparticles, the particulate silica shell inhibiting aggregation of the particulate silica coated hydrogel microparticles in an aqueous medium and being permeable to allow release of agents from the hydrogel inner core.

12. The method of claim 10, wherein the organic solvent comprises a plant derived oil.

13. The method of claim 10, wherein a solvent that is mixable with both phases of the Pickering emulsion is used to extract water.

14. The method of claim 10, wherein the particulate silica coated hydrogel microparticles have an average diameter of about 1 μm to about 500 μm and the silica nanoparticles have an average diameter of about 1 nm to about 999 nm.

15. The method of claim 10, wherein particulate silica coated hydrogel microparticles are isolated from the organic solvent by filtration.

16. The method of claim 10, wherein the gelatin is at least partially crosslinked.

17. The method of claim 10, further comprising combining the particulate silica coated hydrogel microparticles with a plurality of cells.

* * * * *